United States Patent [19]
Jahnsson

[11] Patent Number: 6,105,574
[45] Date of Patent: Aug. 22, 2000

[54] SINGLE DOSE INHALER II

[75] Inventor: Magnus Jahnsson, Södertälje, Sweden

[73] Assignee: Astra Aktiebolag, Sodertalje, Sweden

[21] Appl. No.: 09/029,874

[22] PCT Filed: Jan. 29, 1998

[86] PCT No.: PCT/SE98/00130

§ 371 Date: Mar. 2, 1998

§ 102(e) Date: Mar. 2, 1998

[87] PCT Pub. No.: WO98/34662

PCT Pub. Date: Aug. 13, 1998

[30] Foreign Application Priority Data

Feb. 7, 1997 [SE] Sweden .................. 9700422

[51] Int. Cl.⁷ .................. A61M 15/00; A61M 16/00; B05D 7/14; B65D 83/06

[52] U.S. Cl. .................. 128/203.15; 128/203.21

[58] Field of Search .................. 128/203.21, 203.15, 128/200.23, 203.12, 200.14, 200.24, 204.25, 200.18; 604/58

[56] References Cited

FOREIGN PATENT DOCUMENTS

WO93/17728  9/1993  WIPO .
WO95/03846  2/1995  WIPO .
WO96/22802  8/1996  WIPO .

*Primary Examiner*—John G. Weiss
*Assistant Examiner*—Joseph F. Weiss, Jr.
*Attorney, Agent, or Firm*—Fish & Richardson P.C.

[57] ABSTRACT

A generally flat, elongate inhaler is disclosed. The inhaler has a bend or a projection in its body that provides a guide to the user as to how far the inhaler should be inserted into the mouth.

16 Claims, 4 Drawing Sheets

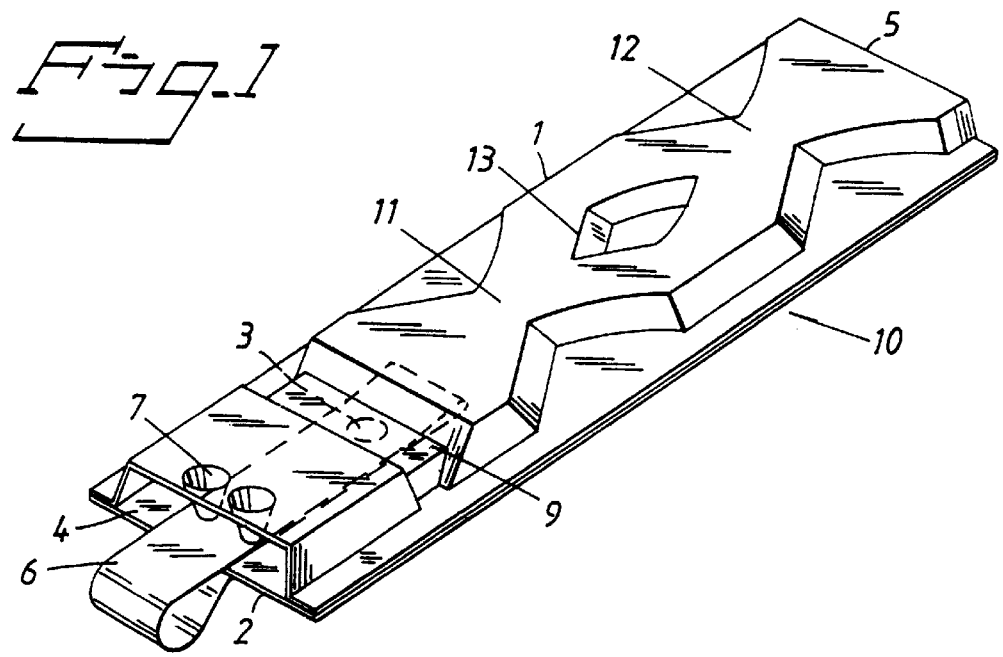
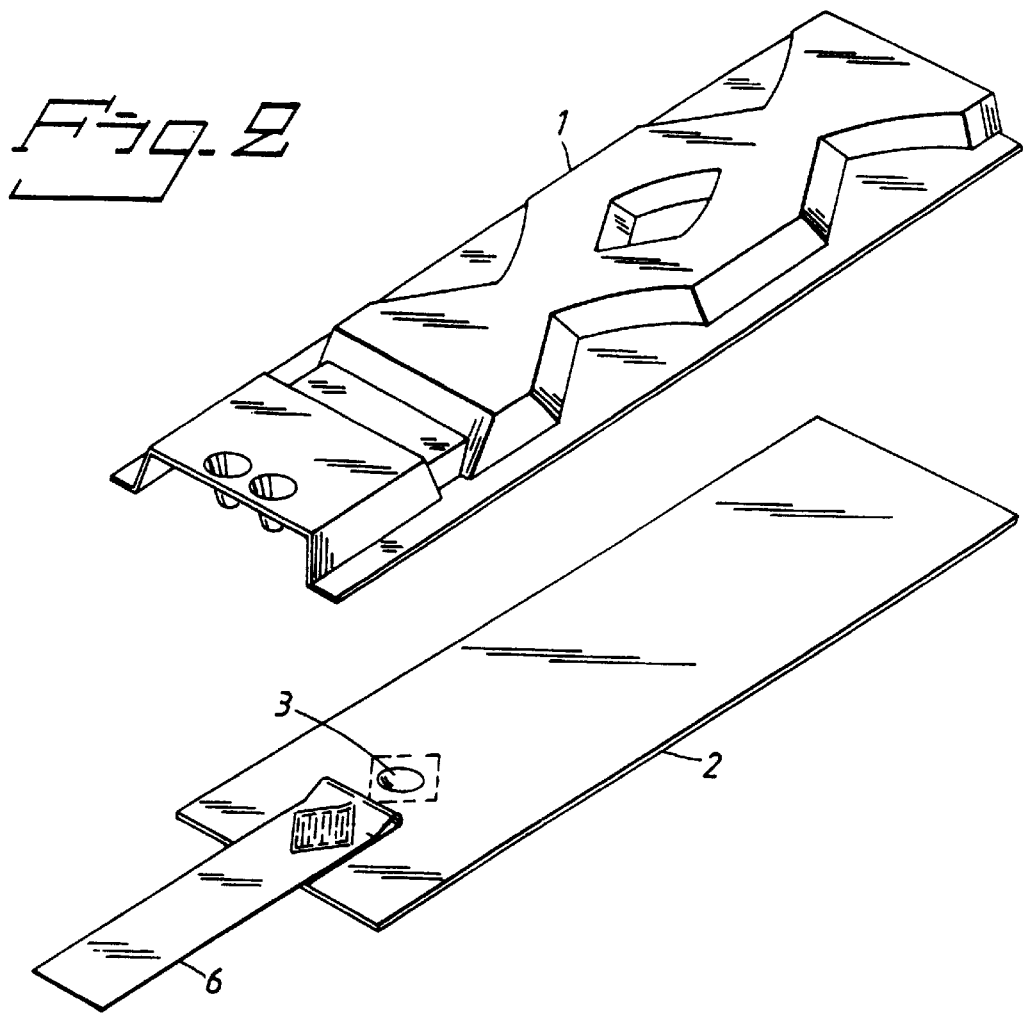

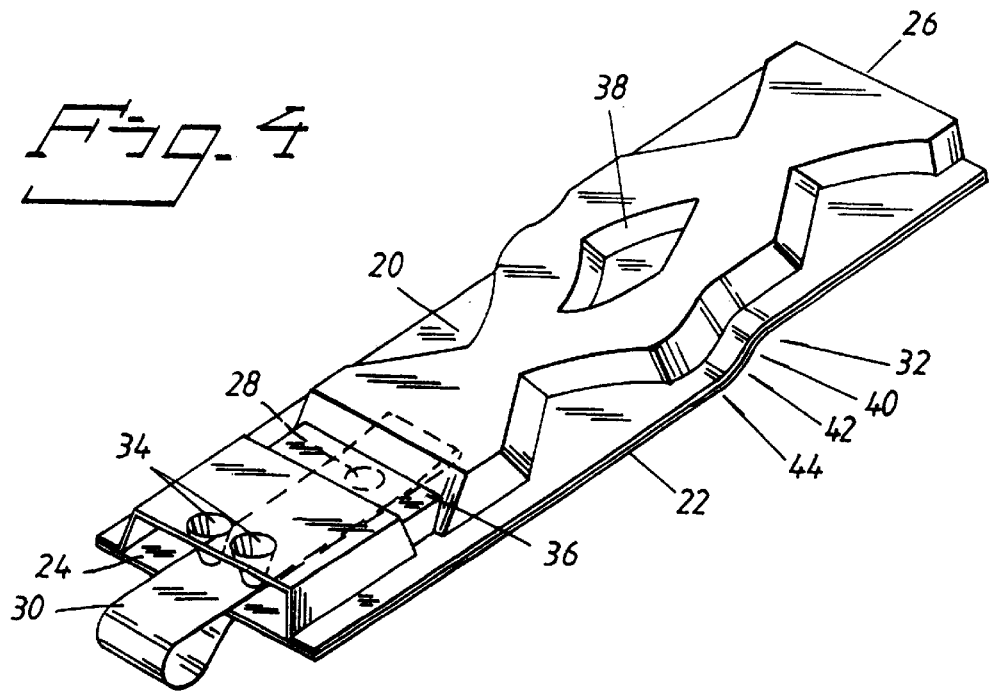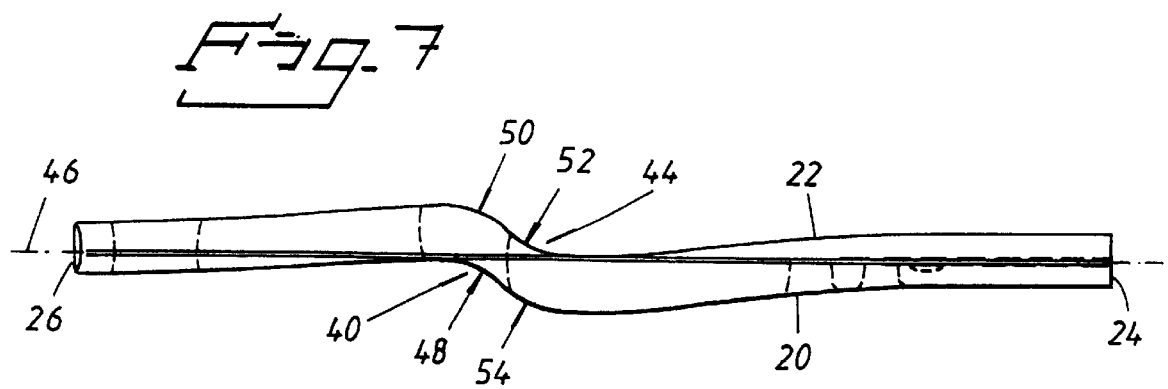

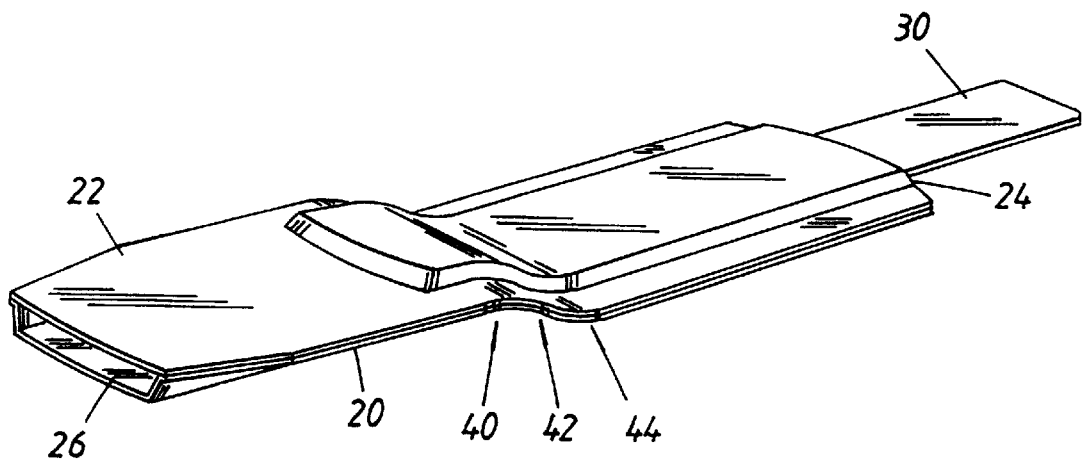
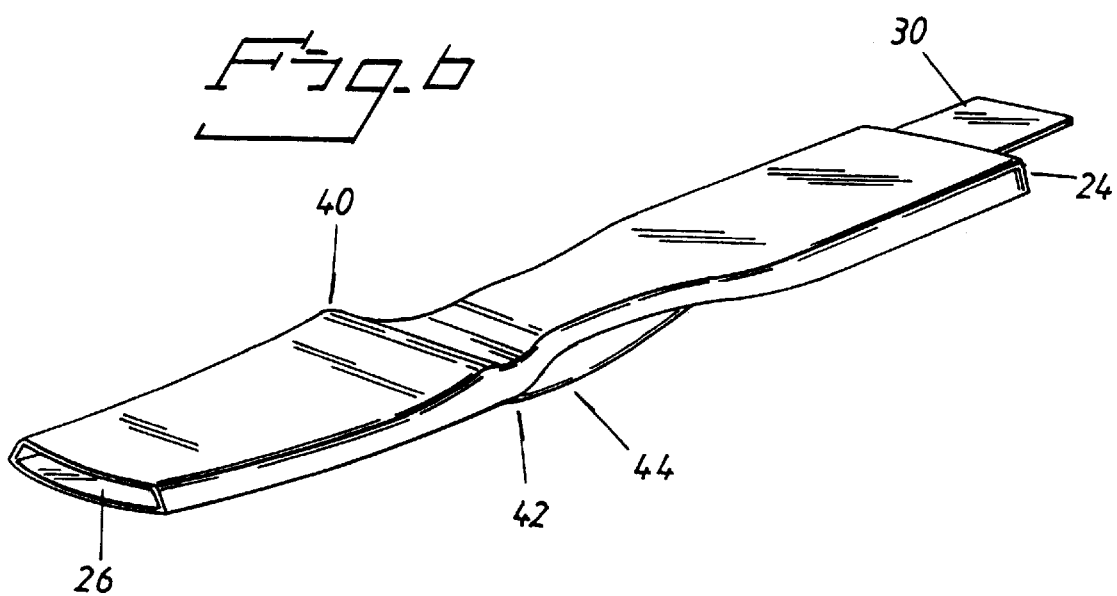

SINGLE DOSE INHALER II

BACKGROUND

The present invention relates to a disposable inhaler, particularly for administering powder by inhalation.

Previously, as described in WO93/17728 and illustrated in FIGS. 1 to 3 of the accompanying drawings, there was known a disposable inhaler constructed from two parts 1 and 2. The lower part 2 includes a recesses 3 in which a dose of powder is stored and the two parts together define a channel through which a stream of air may be drawn by a user from an air inlet 4 to a mouthpiece 5. A tape 6 is provided to cover the recesses 3 and is additionally bent around the outside of the part 2 to cover an aperture 8 in the bottom of the recess 3. In use, the tape 6 is pulled away from the lower part 2 so as to expose both the aperture 8 and the recess 3. Projections 7 are provided to keep the loose tape out of the way of the air flow and a depression 9 directs the air flow to pick up the powder in the recess 3 more effectively. The channel defined by parts 1 and 2 also includes a deagglomeration section 10 having a section inlet 11, a section outlet 12 and a divider 13. The divider 13 splits the stream of air into two flow paths and powder is caused to impact on internal surfaces. In this way, powder is effectively deagglomerated.

In use, a patient inhales through the mouthpiece 5 causing an air stream to pick up the powder stored in recess 3. As the air/powder mixture flows through the inhaler, powder is deagglomerated, then passes out of the mouthpiece 5 and into the lungs of the patient.

An object of the present invention is to simplify use of the inhaler such that it is more difficult to use the inhaler incorrectly.

SUMMARY OF THE INVENTION

The present invention is based on a recognition that it is possible that a user will not insert an inhaler, such as illustrated in FIGS. 1 to 3, sufficiently far into his or her mouth. This is in contrast to many other types of inhaler where mouthpieces are provided to give the user an indication of how far the inhaler should be inserted to thereby prevent the inhaler being inserted too far. The present invention recognises that, with small flat inhalers of the type illustrated in FIGS. 1 to 3, it is important that the inhaler outlet passes beyond the tongue, whereas for other larger types of inhaler, when the mouth is opened sufficiently wide to insert the inhaler, the tongue naturally moves out of the way of the flow of air from the inhaler to the lungs.

According to the present invention, there is provided a method of indicating to a user how far to insert into the mouth an inhaler having a body extending in a first direction between an air inlet and an air/powder outlet, the outer cross-section of the body at substantially every position along the length of the body being elongate in a second direction substantially perpendicular to said first direction, the method comprising displacing the body at a predetermined distance from the air/powder outlet in a third direction perpendicular to said first and second directions.

According to the present invention there is also provided an inhaler for administering powder by inhalation, the inhaler comprising:

a body extending in a first direction between an air inlet and an air/powder outlet, the outer cross-section of the body at substantially every position along the length of the body being elongate in a second direction substantially perpendicular to said first direction; wherein at a predetermined distance from the air/powder outlet, the body is displaced in a third direction perpendicular to said first and second directions so as to provide a guide to the user as to how far the body should be inserted into the mouth of the user.

In this way, the overall construction, simplicity and effectiveness of the inhaler remains unchanged and yet it is immediately apparent to the user to what extent the inhaler should be inserted into his or her mouth. In particular, where the body of the inhaler is displaced downwardly, it will be immediately apparent to the user that the inhaler should be inserted in to his or her mouth until that downward displacement of the body lies immediately adjacent his or her lower lip.

In this way, it is ensured that the outlet of the inhaler is above the tongue, such that the air powder mixture will travel down into the lungs of the user, rather than be deposited on his or her tongue.

Preferably, the body is shaped such that a plane exists wholly within the body.

In this way, despite the displacement in the body, it is still possible to construct the body from two parts, each having respective portions lying in respect planes for joining together.

Preferably, at a second predetermined distance further than said first predetermined distance from the outlet, the body is bent in a direction opposite to said third direction.

In this way, the inhaler is formed with a gentle S-bend along its length and retains its generally flat planar elongate shape.

Although not directly relevant to the present invention, it should be noted that medicaments suitable for administration by an inhaler using the present invention are any which may be delivered by inhalation. Suitable inhalable medicaments may include for example β2-adrenoreceptor agonists for example salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators for example ipratropium bromide and the like; glucocorticosteroids for example beclomethasone, fluticasone, budesonide, tipredane, dexamethasone, betamethasone, fluocinolone, triamcinolone acetonide, mometasone, and the like, and their pharmacologically acceptable esters and salts; anti-allergic medicaments for example sodium cromoglycate and nedocromil sodium; expectorants; mucolytics; antihistamines; cyclooxygenase inhibitors; leukotriene synthesis inhibitors; leukotriene antagonists, phospholipase-A2 (PLA2) inhibitors, platelet aggregating factor (PAF) antagonists and prophylactics of asthma; antiarrhythmic medicaments, tranquilisers, cardiac glycosides, hormones, antihypertensive medicaments, antidiabetic- antiparasitic- and anticancer-medicaments, sedatives and analgesic medicaments, antibiotics, antirheumatic medicaments, immunotherapies, antifungal and antihypotension medicaments, vaccines, antiviral medicaments, proteins, polypeptides and peptides for example peptide hormones and growth factors, polypeptides vaccines, enzymes, endorphines, lipoproteins and polypeptides involved in the blood coagulation cascade, vitamins and others, for example cell surface receptor blockers, antioxidants, free radical scavengers and organic salts of N,N' diacetylcystine.

The present invention will be more clearly understood from the following description, given by way of example only, with reference to the accompanying drawings.

BRIEF DESCRIPTION OF THE DRAWINGS

FIG. 1 illustrates a previous inhaler;

FIG. 2 illustrates the previous inhaler of FIG. 1 separated into two parts;

FIG. 4 illustrates an inhaler similar to that of FIG. 1 embodying the present invention;

FIG. 5 illustrates an embodiment of the present invention;

FIG. 6 illustrates an embodiment of the present invention; and

FIG. 7 illustrates schematically a cross-section of an embodiment of the present invention.

DESCRIPTION OF THE PREFERRED EMBODIMENTS

Figure 3A:
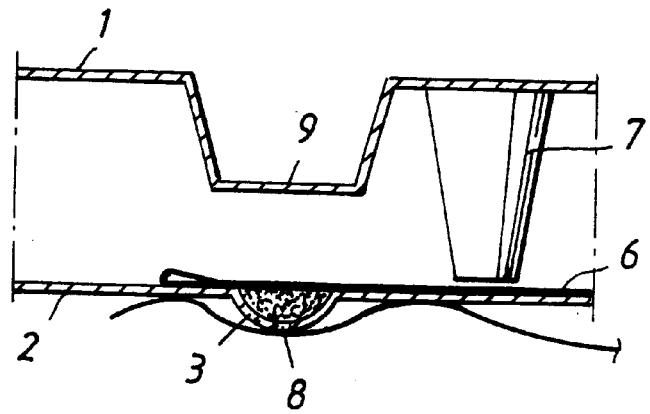
FIGS. 3a, 3b and 3c illustrate a cross-section of the inhaler of FIG. 1.
Figure 3B:
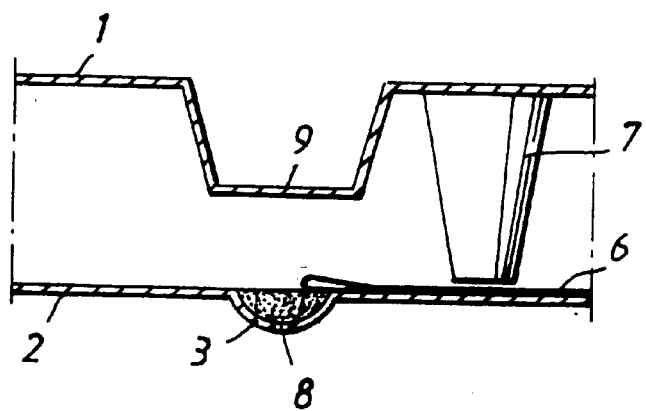
Figure 3C:
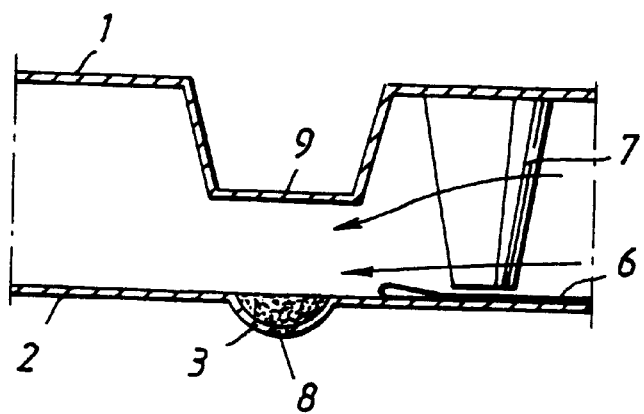

The inhaler illustrated in FIG. 4 is similar to that illustrated in FIG. 1, but at a position upstream of the inhaler outlet, the inhaler body is displaced downwardly.

The inhaler is constructed from a first part 20 and a second part 22. The first part 20 and second part 22 are preferably moulded from a transparent plastics material such that the channels of the inhaler may be inspected before and after use. The first part 20 and second part 22 are joined together to form the inhaler illustrated in FIG. 4.

The inhaler has an air inlet 24 and an outlet 26. Furthermore, like the inhaler of FIG. 1, the second part 22 includes a depression 28 for containing a dose of medicament, preferably in powdered form.

A tape 30 is provided to seal the depression 28 and extends out of the air inlet 24.

In use, the tape 30 is pulled out of the air inlet 24 so as to peel it away from the depression 28 and expose the powder contained in that depression. The outlet 26 is then placed into the mouth of the patient and the patient inhales through the inhaler. When the patient inhales, air is drawn in through the air inlet 24 and picks up the powder from the depression 28. The air powder mixture is drawn through the inhaler through a deagglomeration section 32 and out of the outlet 26.

In order to prevent the loose tape 30 from impeding the air flow into the air inlet 24, projections 34 are provided to hold the loose tape close to the inner surface of the lower part 22.

As illustrated, a restriction 36 is provided in the inhalation channel at the position of the depression 28. This is to direct the air flow down towards the depression 28 so as to assist in ensuring that the powder in the depression 28 joins the air flow through the inhaler.

The deagglomeration section 32 is provided to break down any larger powder particles into their constituent fine powder particles. In particular, the deagglomeration section 32 is provided with a divider 38 which divides the air stream into two paths and causes powder carried by the air stream to impact with internal walls of the inhaler.

As illustrated, the inhaler of FIG. 4 has a generally flat elongate form. This makes it easy to store and pleasing to patients. It may be constructed with a relatively small overall size which is advantageous to patients, particularly those who have to carry a number of such inhalers with them on a day to day basis. However, although the elongate cross section and outlet are very pleasing and advantageous to the user, since they may very easily be inserted to the mouth, it is important that the outlet 26 of the inhaler extends beyond the tongue.

With an inhaler of this form, i.e. one which extends in a generally first direction between the air inlet 24 and the outlet 28 and has a generally flat construction such that it extends in an elongate manner in a direction perpendicular to the first direction, a patient does not open his or her mouth to any great extent, such that the tongue is not naturally moved down away from the flow of air between the mouth and the lungs. Thus, as illustrated in FIG. 4, unlike previous inhalers of this general form, the inhaler is not completely flat along its length, but, at position 40, is deflected downwards, such that it is displaced in a third direction perpendicular to both the first and second directions. This deflection or displacement provides a downwardly extending wall 42, which, in use, may be pressed against the lower lip of the user. In this way, the user can assuredly insert the inhaler into his or her mouth by the correct amount. Indeed, because of the shape of the inhaler, it will feel strange to insert the inhaler by less than the correct amount.

Thus, in use, the inhaler will be inserted with the outlet 26 over and clear of the user's tongue, rather than a position where the user's tongue could still impede the flow of air/powder from the outlet 26 into his or her lungs.

Since it is desirable that the inhaler retains its generally flat form, at position 44, the inhaler is deflected back upwardly such that it is displaced or bent in a direction opposite to the third direction. In this way, the inhaler may have the required function and yet retain a pleasing gentle S-bend form.

Clearly, as described above, the present invention applies to any inhaler having the generally flat form described above, in particular inhalers where the portion to be inserted into the mouth is generally flat with a shallow elongate cross-section. It is not essential to the invention how medicament is stored or released into the inhalation channel of the inhaler, nor is it essential to the invention that, where the medicament is in powdered form, it is deagglomerated as described above. Nevertheless, it is particularly advantageous with dry powder inhalers of the general form discussed above.

FIGS. 5 and 6 illustrate two other inhalers embodying the present invention.

FIG. 7 illustrates a cross-section of an inhaler according to the present invention. As illustrated, a plane 46 exists which passes within the inhaler. Shaping the inhaler with such a plane is highly advantageous, since, as illustrated, the inhaler can be formed from first 20 and second 22 parts which can still be joined at a flat surface. This makes the moulding and construction steps much more straightforward.

FIG. 7 also illustrates some preferred dimensions or inhalers of this type. In general, such inhalers should be between 50 mm and 120 mm in length, 3 mm and 20 mm in height and 10 mm and 40 mm in width. More preferably, they should be between 60 mm and 90 mm in length, 3 mm and 12 mm in height and 12 mm and 30 mm in width or in the region or more preferably still, they should be in the region of 80 mm in length, 5 mm in height and 20 mm in width. Of course, the width to height ratio is of some importance and should be between 2 to 13, 3 to 10 or preferably in the region of 4. Preferably, at position 40, there is an inner radius of curvature 48 of approximately 5 mm and an outer radius of curvature 50 of approximately 8 mm. Similarly, at position 44, there is an inner radius of curvature 52 of approximately 5 mm and an outer radius of curvature 54 of approximately 8 mm.

To obtain the correction length of insertion of the outlet 26 into the mouth of a patient, the downwardly extending wall 42 should occur at approximately 30 mm from the outlet 26. It may be sufficient to have the downward deflection at a position in the region of 20 mm to 60 mm, with increasing preference for the ranges 20 mm to 50 mm, 25 mm to 45 mm and 25 mm to 35 mm.

What is claimed is:

1. An inhaler for administering powder by inhalation, the inhaler comprising:

a body extending in a first direction between an air inlet and an air/powder outlet, an outer cross-section of the body at substantially every position along a length of the body being elongate in a second direction perpendicular to said first direction;

wherein, at a predetermined distance from the air/powder outlet, the body is displaced in a third direction perpendicular to said first and second directions, forming a wall, the wall in use contacting a lip of the user so as to provide a guide to the user as to how far the body should be inserted into a mouth of the user wherein, at a second predetermined distance further than said first predetermined distance from the outlet, the body is displaced in a direction opposite to said third direction.

2. An inhaler according to claim 1 wherein the body forms a generally S-shaped bend along its length.

3. An inhaler according to claim 1, wherein the body is shaped such that a plane exists wholly within the body.

4. An inhaler according to claim 1 wherein, where the body is displaced in the third direction, the outer surface of the body bends with an inner radius of curvature of approximately 5 mm and an outer radius of curvature of approximately 8 mm.

5. An inhaler according to claim 1, wherein said predetermined distance from the outlet is 20 mm to 60 mm.

6. An inhaler according to claim 5 wherein said predetermined distance from said outlet is about 30 mm.

7. The inhaler of claim 5 wherein said predetermined distance from the outlet is 20 mm to 50 mm.

8. The inhaler of claim 7 wherein said predetermined distance is 25 mm to 45 mm.

9. The inhaler of claim 1 wherein the body includes a first part and a second part, the first and second parts defining an inhalation channel therebetween.

10. An inhaler for administering powder by inhalation, the inhaler comprising: a body extending in a first direction between an air inlet and an air/powder outlet, an outer cross-section of the body at substantially every position along a length of the body being elongate in a second direction perpendicular to said first direction;

wherein, at a predetermined distance from the air/powder outlet, the body is displaced in a third direction perpendicular to said first and second directions, forming a wall, the wall in use contacting a lip of the user so as to provide a guide to the user as to how far the body should be inserted into a mouth of the user;

wherein the body includes a first part and a second part, the first and second parts defining an inhalation channel therebetween;

wherein either the first part or the second part defines a recess that contains a dose of powder, the dose of powder comprising a pharmaceutically active substance.

11. The inhaler of claim 10 wherein the substance is systemically active.

12. An inhaler for administering powder by inhalation, the inhaler comprising:

a body extending in a first direction between an air inlet and an air/powder outlet, an outer cross-section of the body at substantially every position along a length of the body being elongate in a second direction perpendicular to said first direction;

wherein, at a predetermined distance from the air/powder outlet, the body is displaced in a third direction perpendicular to said first and second directions, forming a wall, the wall in use contacting a lip of the user so as to provide a guide to the user as to how far the body should be inserted into a mouth of the user wherein the body defines an inhalation channel extending from the air inlet to the air/powder outlet, the inhalation channel having an upper wall and a lower wall, the upper and lower walls extending in both said first and said second directions, wherein a plane defined by said first and second directions passes through said channel without contacting the upper or the lower wall.

13. An inhaler for administering powder by inhalation, the inhaler comprising: a body extending in a first direction between an air inlet and an air/powder outlet, an outer cross-section of the body at substantially every position along a length of the body being elongate in a second direction perpendicular to said first direction;

wherein, at a predetermined distance from the air/powder outlet, the body is displaced in a third direction perpendicular to said first and second directions, forming a wall, the wall in use contacting a lip of the user so as to provide a guide to the user as to how far the body should be inserted into a mouth of the user;

wherein said predetermined distance is 25 mm to 35 mm.

14. A method of indicating to a user how far to insert into a mouth of the user an inhaler having a body extending in a first direction between an air inlet and an air/powder outlet, an outer cross-section of the body at substantially every position along a length of the body being elongate in a second direction substantially perpendicular to said first direction, the method comprising:

displacing the body at a predetermined distance from the air/powder outlet in a third direction perpendicular to said first and second directions so as to form a wall, the wall during use contacting a lip of the user thereby indicating to the user how far the body should be inserted into the user's mouth further comprising inserting the body into the user's mouth such that the wall contacts a lip of the user, and the outlet is located beyond a tongue of the user.

15. An inhaler for administering powder by inhalation the inhaler comprising:

a first end sized and shaped to fit within a user's mouth, the first end defining an air/powder outlet;

a second end defining an air inlet;

a generally flat, elongate body that defines an inhalation channel between the inlet and the outlet, the body including a projection spaced a predetermined distance from the outlet, the predetermined distance being sufficiently long such that inserting the first end into a user's mouth until the projection contacts the user's lip locates the outlet beyond the user's tongue, thereby preventing the user's tongue from blocking delivery of the powder.

16. The inhaler of claim 15 wherein the predetermined distance is 20–50 mm.

* * * * *